United States Patent [19]

Ono et al.

[11] Patent Number: 4,537,989

[45] Date of Patent: Aug. 27, 1985

[54] IMINO-BICYCLO (3.3.0) OCTANE DERIVATIVES

[75] Inventors: Keiichi Ono, Osaka; Akihiko Sugie; Masami Muraoka, both of Toyonaka; Michihiro Yamamoto, Nishinomiya, all of Japan

[73] Assignee: Sumitomo Chemical Company, Limited, Osaka, Japan

[21] Appl. No.: 485,587

[22] Filed: Apr. 15, 1983

[30] Foreign Application Priority Data

Apr. 26, 1982 [JP] Japan .................................. 57-71071

[51] Int. Cl.³ .................... C07C 131/02; A61K 31/19; A61K 31/195; A61K 31/215
[52] U.S. Cl. .................................... 562/501; 560/35; 560/107; 560/108; 560/116; 560/119; 560/251; 560/252; 562/440; 562/498; 564/167; 564/188; 514/822; 514/925; 544/149; 544/152; 544/165; 544/374; 544/391; 546/205; 546/206; 548/517; 548/540; 549/414; 549/415; 549/421; 549/422; 549/473; 549/475
[58] Field of Search ...................... 562/440, 498, 501; 424/319; 544/149, 152, 165, 374, 391; 546/205, 206; 548/517, 540; 549/414, 415, 421, 422, 473, 475; 560/35, 107, 108, 116, 119, 251, 252; 564/167, 188

[56] References Cited

U.S. PATENT DOCUMENTS 4,423,067  12/1983  Skuballa et al. .................... 562/498
4,423,068  12/1983  Li et al. .............................. 562/501

FOREIGN PATENT DOCUMENTS 0015653  9/1980  European Pat. Off. ............. 562/501
56-5456  1/1981  Japan .................................. 424/317

Primary Examiner—Natalie Trousof
Assistant Examiner—Patricia M. Scott
Attorney, Agent, or Firm—Stevens, Davis, Miller & Mosher

[57] ABSTRACT

A compound of the formula

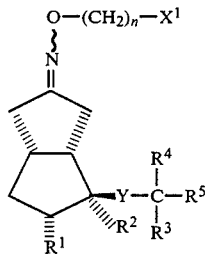

wherein $X^1$ is a free or an esterified carboxyl group, or a group of the formula:

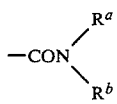

($R^a$ and $R^b$ are each independently a hydrogen atom, a $C_1$-$C_4$ alkyl group, a $C_3$-$C_7$ cycloalkyl group, a benzyl group, a phenyl group, a phenyl group substituted with a halogen atom or a $C_1$-$C_4$ alkyl group, or, when taken together with the adjacent nitrogen atom to which they are attached, they represent a 5 to 7 membered saturated heterocyclic group), Y is a group of the formula:

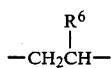

($R^6$ is a hydrogen atom or a $C_1$-$C_4$ alkyl group) or

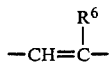

($R^6$ is as defined above), $R^1$ is a hydrogen atom, a hydroxyl group or a protected hydroxyl group, $R^2$ is a hydrogen atom or $R^1$ and $R^2$, when taken together, mean a single linkage to form a double bond between the carbon atoms which they are linked, $R^3$ is a hydroxyl group or a protected hydroxyl group, $R^4$ is a hydrogen atom or a $C_1$-$C_4$ alkyl group, $R^5$ is a hydrogen atom, a $C_3$-$C_8$ alkynyl group, a $C_3$-$C_8$ alkenyl group, a $C_1$-$C_8$ alkyl group, a $C_3$-$C_7$ cycloalkyl group, a hydroxy $C_1$-$C_8$ alkyl group or a group of the formula: —(CH$_2$)$_m$—B (m is 1 or 2 and B is a $C_1$–$C_4$ alkoxy, a $C_3$-$C_7$ cycloalkyl, or a phenyl or phenoxy group optionally substituted with a halogen atom, a $C_1$-$C_4$ alkyl group, a trifluoromethyl group or a $C_1$-$C_4$ alkoxy group), and n is 2 or 3; or a non-toxic pharmaceutically acceptable salt thereof. Said compounds have strong anti-cancer activity and are useful in treatment of a cancer.

5 Claims, No Drawings

IMINO-BICYCLO (3.3.0) OCTANE DERIVATIVES

The present invention relates to novel bicyclooctane compounds, their production and use.

More particularly, this invention relates to novel bicyclooctane compounds, to a pharmaceutical composition containing at least one of the bicyclooctane compounds and to a process for production thereof.

The novel bicyclooctane compounds provided by the present invention are those represented by the formula [I]:

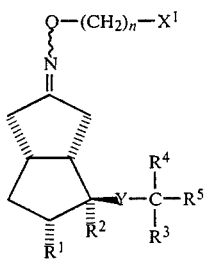

wherein $X^1$ is a free or an esterified carboxyl group, or a group of the formula:

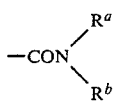

($R^a$ and $R^b$ are each independently a hydrogen atom, a $C_1$–$C_4$ alkyl group, a $C_3$–$C_7$ cycloalkyl group, a benzyl group, a phenyl group, a phenyl group substituted with a halogen atom or a $C_1$–$C_4$ alkyl group, or, when taken together with the adjacent nitrogen atom to which they are attached, they represent a 5 to 7 membered saturated heterocyclic group), Y is a group of the formula:

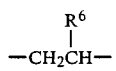

($R^6$ is a hydrogen atom or a $C_1$–$C_4$ alkyl group) or

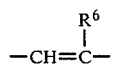

($R^6$ is as defined above),
$R^1$ is a hydrogen atom, a hydroxyl group or a protected hydroxyl group, $R^2$ is a hydrogen atom or $R^1$ and $R^2$, when taken together, mean a single linkage to form a double bond between the carbon atoms to which they are linked, $R^3$ is a hydroxyl group or a protected hydroxyl group, $R^4$ is a hydrogen atom or a $C_1$–$C_4$ alkyl group, $R^5$ is a hydrogen atom, a $C_3$–$C_8$ alkynyl group, a $C_3$–$C_8$ alkenyl group, a $C_1$–$C_8$ alkyl group, a $C_3$–$C_7$ cycloalkyl group, a hydroxy $C_1$–$C_8$ alkyl group or a group of the formula: —$(CH_2)_m$—B (m is 1 or 2 and B is a $C_1$–$C_4$ alkoxy, a $C_3$–$C_7$ cycloalkyl, or a phenyl or phenoxy group optionally substituted with a halogen atom, a $C_1$–$C_4$ alkyl group, a trifluoromethyl group or a $C_1$–$C_4$ alkoxy group), and n is 2 or 3.

Among the bicyclooctane compounds of the formula [I], the preferred compounds are, with respect to the formula [I], those in which Y is a vinylene group and n is 2.

In the description set forth above, the term "halogen" includes fluorine, chlorine, bromine and iodine; the terms "$C_1$–$C_4$ alkyl" and "$C_1$–$C_4$ alkoxy" mean straight or branched chain alkyl and alkoxy groups having from 1 to 4 carbon atoms (e.g. methyl, ethyl, n-propyl, isopropyl, n-butyl, methoxy, ethoxy, n-propoxy, isopropoxy, n-butoxy, etc.).

The term "$C_1$–$C_8$ alkyl" means a straight or branched chain alkyl group having from 1 to 8 carbon atoms (e.g. methyl, ethyl, n-propyl, isopropyl, n-butyl, isobutyl, n-pentyl, isopentyl, 1-methylpentyl, 2-ethylpentyl, 1,1-dimethylpentyl, 2-methylpentyl, n-hexyl, 2-methylhexyl, etc.); and the terms "$C_3$–$C_8$ alkenyl" and "$C_3$–$C_8$ alkynyl" mean straight or branched chain alkenyl and alkynyl groups having from 3 to 8 carbon atoms (e.g. propenyl, 2-butenyl, 2-pentenyl, 2-hexenyl, 5-heptenyl, 6-methyl-hept-5-enyl, 3-pentenyl, 4-pentenyl, 2-propynyl, 2-butynyl, 2-pentynyl, 3-pentynyl, 4-pentynyl, 5-heptynyl, 6-heptynyl, 1-methyl-3-pentynyl etc.).

The term "$C_3$–$C_7$ cycloalkyl" includes cyclopropyl, cyclobutyl, cyclohexyl, cyclopentyl, cycloheptyl.

The term "esterified carboxyl group" includes $C_1$–$C_4$ alkoxycarbonyl, aryloxycarbonyl (e.g. phenoxycarbonyl, naphthoxycarbonyl), aralkyloxycarbonyl (e.g. benzyloxycarbonyl, phenethyloxycarbonyl), ($C_1$–$C_4$ alkoxy)methoxycarbonyl, ($C_2$–$C_5$ alkanoyloxy)methoxycarbonyl (e.g. acetoxymethoxycarbonyl, pivaloyloxymethoxycarbonyl), ($C_3$–$C_7$ cycloalkoxy)carbonyl, arylcarbonylmethoxycarbonyl and (hydroxy $C_1$–$C_4$ alkoxy)carbonyl.

The term "5 to 7 membered saturated heterocyclic group" includes piperidino, pyrrolidino, homopiperidino, morpholino, piperazino, N-($C_1$–$C_4$)alkylpiperazino.

The term "protected hydroxy group" means a hydroxy group protected with $C_1$–$C_4$ alkanoyl, benzoyl, substituted benzoyl, tetrahydropyranyl, tetrahydrofuryl or ($C_1$–$C_4$ alkoxy)alkyl.

A tremendous amount of research in synthetic organic chemistry, pharmacology and clinical medicine of prostaglandins has been performed since discovery of prostaglandins.

In 1976, J. Vane of the Wellcome Foundation reported on the isolation and biological effects of prostacyclin [prostaglandin $I_2$]. [S. Moncada, R. Gryglewski, S. Bunting, and J. R. Vane, Nature (London), 263, 663 (1976)].

Prostaglandin $I_2$[II], which is shown below, has several excellent pharmacological activities, for example, hypotensive, vasodilating, antiallergic, antiulcerogenic and antithrombotic, and is expected to be useful in treating asthma, ulcers, thrombosis or hypertension.

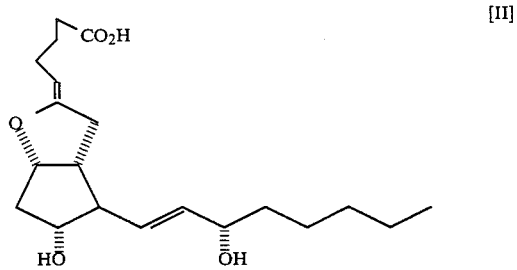

However, prostaglandin $I_2$ (referred to as "$PGI_2$", hereinafter) may not be used as a medicine due to its instability and variety of pharmacological actions.

As the result of a study, it has now been found that the novel bicyclooctane compounds [I] of the present invention and their non-toxic pharmaceutically acceptable salts have antithrombotic, antihypertensive or antisecretory action and are useful in the treatment of ulcers, thrombosis hypertension. In addition, the undersirable chemical instability of $PGI_2$ is absent in the compounds [I] of the present invention.

Accordingly, a basic object of the present invention is to provide novel and stable bicyclooctane compounds [I] having excellent pharmacological activity.

Another object of the present invention is to provide a process for producing those compounds [I]. A further object of the present invention is to provide a pharmaceutical composition containing a compound of the formula [I]. These and other objects will be apparent to those skilled in the art to which the present invention pertains from the foregoing and subsequent descriptions.

The novel bicyclooctane compound [I] of the invention can be prepared by the following two methods.

(1) The bicyclooctane compound of the formula [I]

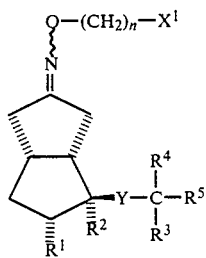

wherein $X^1$, Y, $R^1$, $R^2$, $R^3$, $R^4$, $R^5$ and n are each as defined above, can be prepared from a carbonyl compound of the formula [III]:

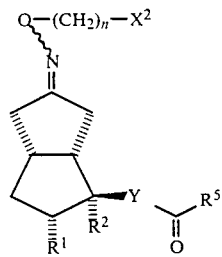

wherein $X^2$ is a free or esterified carboxyl group or a cyano group and Y, $R^1$, $R^2$, $R^5$ and n are each as defined above, by reacting the latter with a reducing agent or an organometalic compound of the formula:

$$M-R^7 \qquad [IV]$$

wherein $R^7$ is a $C_1$-$C_4$ alkyl group and M is a lithium atom or —Mg halo (halo is a halogen atom); optionally followed by hydrolysis of a cyano or ester group, esterification of a carboxyl group, amidation of a free or esterified carboxyl group, reduction of a vinylene group, protection of a hydroxyl group and/or deprotection of a protected hydroxyl group.

(2) The bicyclooctane compounds [I] can be also prepared from an oxime compound of the formula:

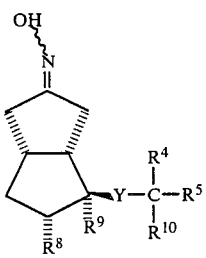

wherein $R^4$, $R^5$ and Y are each as defined above and $R^8$ is a hydrogen atom or a protected hydroxy group, $R^9$ is a hydrogen atom, or $R^8$ and $R^9$, when taken together, mean a single linkage to form a double bond between the carbon atoms to which they are linked, and $R^{10}$ is a protected hydroxy group; by reacting the latter with β-propiolactone, acrylonitril, acrylic acid, acrylic acid ester, γ-halogenobutyronitril, β-halogenopropionic acid or β-halogenopropionic acid ester; optionally followed by hydrolysis of a cyano or ester group, esterification of a carboxyl group, amidation of a free or esterified carboxyl group, reduction of a vinylene group, protection of a hydroxy group and/or deprotection of a protected hydroxy group.

The sequence of the steps from the carbonyl compound [III] or the oxime [V] to the bicyclooctane compound [I] as stated above may be represented by the following schema:

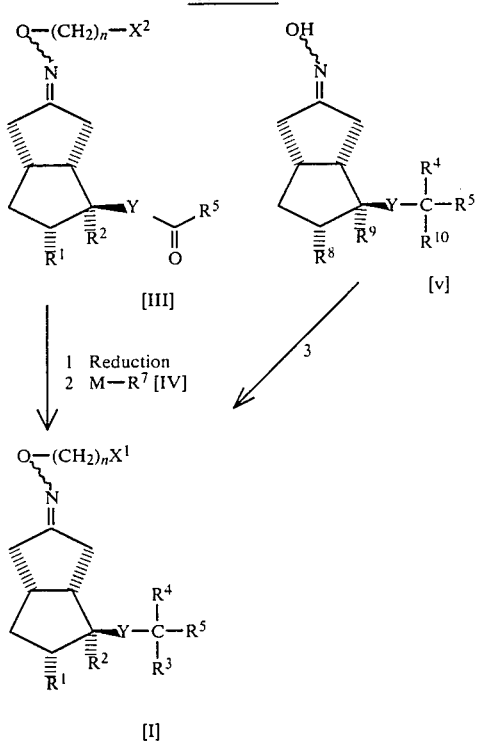

Step 1

(Production of the bicyclooctane compound [I] from the carbonyl group [III] by reduction of a carbonyl group).

The carbonyl compound [III] can be converted into the corresponding alcohol compound by reacting the former with a reducing agent in an inert solvent (e.g. THF, ether, dimethoxyethane, pentane, hexane, benzene, toluene, metanol, ethanol) at a temperature in the range from −70° C. to room temperature.

As the reducing agent, there may be used for example trialkylborohydride (e.g. lithium triisobutyl borohydride), bis(2,4,6-tri-tert-butylphenoxy)aluminum hydride, sodium borohydride, zinc borohydride, diisobutyl aluminum hydride, diisobutyl aluminum-2,6-di-t-butyl-4-methylphenol, ethoxy 1,1′-binaphthyl-2,2′-dioxyaluminum lithium hydride.

The protection and deprotection of a hydroxyl group can be carried out by conventional procedures [Protective Group in Organic Chemistry, Edited by J. F. W. McOmie (1973) 95–143].

The reduction of a vinylene group can be accomplished by catalytic hydrogenation in an inert solvent (e.g. alkanol, aqueous alkanol) at a temperature in the range from 0° C. to room temperature.

Step 2

(Reaction of a carbonyl group [III] with an organometalic compound [IV].)

The carbonyl compound [III] can be converted into the corresponding alcohol compound by reacting the former with an organometalic compound [IV] in an inert solvent (e.g. ether, THF, dioxane) at a temperature in the range from −70° C. to room temperature. The organometalic compound [IV] can be prepared by conventional procedures.

Step 3

The alkylation of the oxime [V] can be carried out by reacting [V] with an alkylating agent in an inert solvent (e.g. benzene, toluene, xylene, DMF, DMSO, alkanoyl) in the presence of an alkali (e.g. alkali metal hydride, alkali metal amide, alkali metal, alkali metal t-butoxide, alkali hydroxide) at a temperature in the range from 0° C. to the boiling temperature of the solvent.

As the alkylating agent, there may be used for example β-propiolactone, acrylonitril, acrylic acid, acrylic acid ester, γ-halogenobutyronitril, β-halogenopropionic acid and β-halogeno propionic acid ester.

The steps of amidation of a carboxyl group, amidation of a esterified carboxy group, hydrolysis of a cyano group into a carboxyl group, hydrolysis of an esterified carboxyl group and esterification of a carboxyl group may be represented by the following schema:

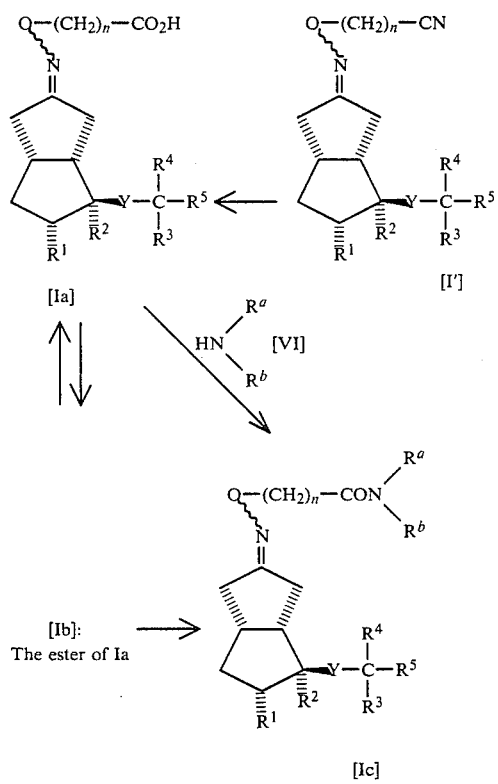

Scheme B

Amidation of a carboxyl group can be carried out by conventional procedures. For instance, it can be accomplished in an inert solvent (e.g. ether, THF) by treating a carboxyl compound [Ia] with an amine [VI] ($R^a$ and $R^b$ are each as defined above) in the presence of a dehydrolyzing agent (e.g. dicyclohexylcarbodiimide) at a temperature in the range from 0° C. to room temperature, or by treating the functionally active derivative (e.g. mixed acid anhydride) of [Ia] with the amine [VI] in an inert solvent (e.g. ether, THF, chloroform) at a temperature in the range from −10° C. to room temperature.

Amidation of an esterified carboxyl group can be carried out by treating an ester compound [Ib] with the amine [VI] in an inert solvent (e.g. DMF, methanol, ethanol, THF) at a temperature in the range from room temperature to the boiling temperature of the solvent.

Hydrolysis of a cyano group into a carboxyl group can be carried out in the presence of an alkali (e.g. sodium hydroxide, potassium hydroxide) in an inert solvent (e.g. aqueous alkanol, DMSO) at a temperature in the range from 30° C. to the boiling temperature of the solvent.

The hydrolysis of the ester compound [Ib] and the esterification of a carboxyl group can be carried out by conventional procedures.

The carbonyl compound [III] used as an intermediate in the present invention can be prepared from a ketone compound [VII] by the process shown in scheme C below.

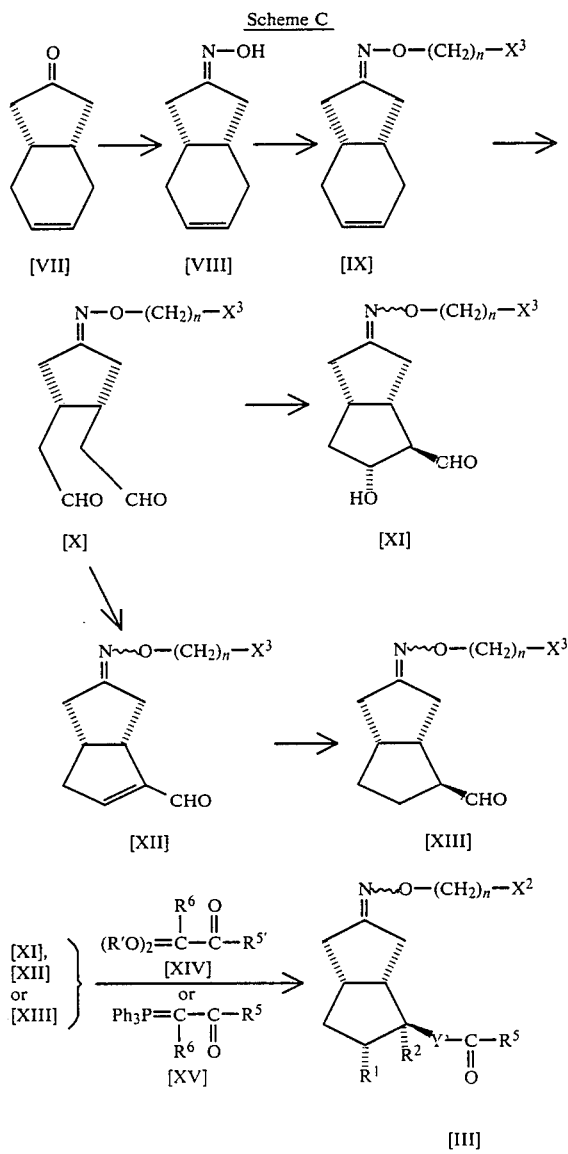

Scheme C

[VII] → [VIII] → [IX] →

[X] → [XI]

[XII] → [XIII]

[XI], [XII] or [XIII]  →  [III]

with [XIV] $(R'O)_2=\overset{R^6}{\underset{|}{C}}-\overset{O}{\underset{||}{C}}-R^{5'}$ or [XV] $Ph_3P=\overset{R^6}{\underset{|}{\underset{R^6}{C}}}-\overset{O}{\underset{||}{C}}-R^5$ In the formulae illustrated in the scheme C, $X^3$ is an esterified carboxyl group or a cyano group, $R^{5'}$ is the same as $R^5$ provided that $R^{5'}$ is not a hydrogen atom, $R'$ is a $C_1$–$C_4$ alkyl group, and $R^1$, $R^2$, $R^5$, $R^6$, $X^2$, Y and n are each as defined above.

The detailed explanation of Scheme C is as follows:

The compound [VIII] is obtained by reacting the ketone [VII] with an acid addition salt of hydroxylamine in the presence of an alkali. The compound [IX] is obtained by reacting the oxime [VIII] with an alkylating agent in an inert solvent (e.g. benzene, toluene, xylene, DMF, DMSO, alkanol) in the presence of an alkali (e.g. alkali metal hydride, alkali metal amide, alkali metal, alkali metal t-butoxide, alkali hydroxide) at a temperature in the range from 0° C. to the boiling temperature of the solvent, optionally followed by esterification. As the alkylating agent, there may be used for example β-propiolactone, acrylonitril, acrylic acid, acrylic acid ester, γ-halogeno-butyronitril, β-halogeno-propionic acid, β-halogeno propionic acid ester. Oxidation of the compound [IX] into the dialdehyde [X] can be accomplished by treatment with sodium metaperiodate in the presence of a catalytic amount of osmium tetroxide in an inert solvent at a temperature in the range from 0° C. to room temperature. Examples of the inert solvent include water, ethers (e.g. dioxane, THF) and aqueous ethers.

The dialdehyde [X] can be also obtained by ozonization of the compound [IX] at a temperature in the range from −80° C. to −30° C., followed by reductive cleavage with dialkyl sulfide, triphenylphosphine, sodium bisulfite, zinc or the like, or by the catalytic hydrogenation in the presence of palladium on charcoal.

Examples of the inert solvent for ozonization include alkanols (methanol, ethanol), halogenated hydrocarbon and ester. Reduction of an ozonide may be accomplished by a per se conventional procedure at a temperature in the range from −30° C. to 0° C.

Aldol condensation of the dialdehyde [X] into an aldole derivative [XI] is carried out in the presence of an acid or a base in an inert solvent (e.g. water, alkanols, aqueous alkanols, ethers, esters) at a temperature in the range from −70° C. to room temperature. Examples of the suitable base are alkali hydroxide (e.g. potassium hydroxide, sodium hydroxide), alkali carbonate and alkali hydrogen carbonate.

The compound [XII] can be obtained by treating the dialdehyde [X] in the presence of an acid or a base in an inert solvent at a temperature in the range from room temperature to the boiling temperature of the solvent.

The compound [XII] can be easily converted into the compound [XIII] by conventional catalytic hydrogenation in the presence of palladium on charcoal, if necessary, followed by epimerization.

The compounds [XI, XII, XIII] can all be easily converted into a carbonyl compound [III] by reacting the former with a compound [XIV] or a compound [XV] in an inert solvent (e.g. dioxane, ether, THF, dimethoxyethane, benzene, toluene, n-hexane, DMSO) at a temperature in the range from −10° to 50° C.; optionally followed by protection of a hydroxy group, hydrolysis of an ester group and/or reduction of a vinylene group.

The selective reduction of a compound [XVI]

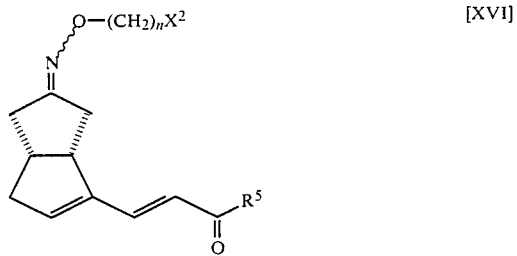

[XVI]

wherein $X^2$ and $R^5$ are each as defined above, into a compound [XVII]

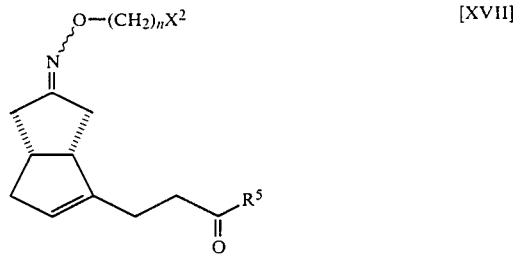

[XVII]

wherein $X^2$ and $R^5$ are each as defined above, can be carried out by reacting the former with trialkylsilane in the presence of titanium tetrachloride in an inert solvent (e.g. halogenated hydrocarbon) at a temperature in the range from $-78°$ C. to $0°$ C.

The oxime compound [V] used as an intermediate in the present invention can be prepared from a ketone compound [XVIII] of the formula

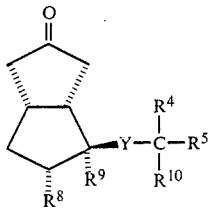

wherein $R^4$, $R^5$, $R^8$, $R^9$, $R^{10}$ and Y are each as defined above by reacting the ketone [XVIII] with an acid addition salt of hydroxylamine in the presence of an alkali (e.g. alkali hydroxide, alkali carbonate) in an inert solvent (e.g. aqueous alkanol, alkanol) at a temperature in the range from $30°$ C. to the boiling temperature of the solvent.

The ketone [XVIII] can be obtained by using a previously described procedure see (European Patent Publication number 36730).

According to the present invention, the four stereoisomers of the formulae:

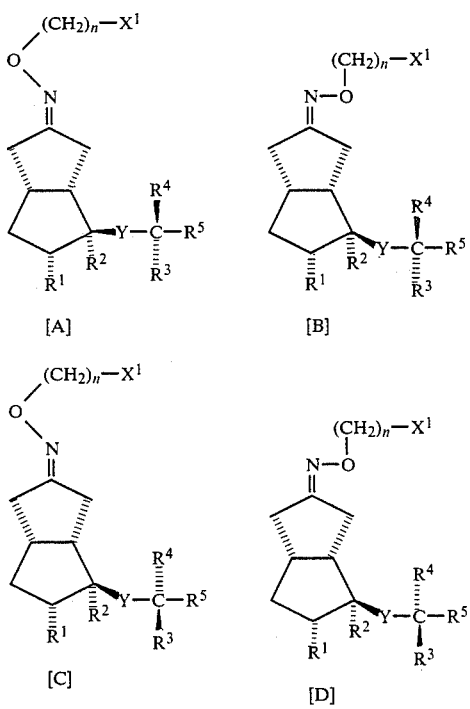

can be prepared.

In general, the bicyclooctane compound [I] can be obtained as a mixture of these stereoisomers which can be easily separated by the conventional procedure with high purity.

If necessary, it is possible to yield selectively the bicyclooctane compound [I] of either one of these stereoisomers by changing the kinds and properties of solvents, reaction temperature, the organometalic compounds [IV] and reducing agents.

Among the bicyclooctane compounds [I] thus obtained, the compound [Ia] can be converted to its pharmacologically acceptable salt form. The pharmaceutically acceptable salts of these bicyclooctane compounds are those formed with pharmaceutically acceptable metal cations such as, sodium, potassium, magnesium and calcium, ammonium or amine cations.

For the preparation of pharmaceutical compositions containing at least one of the bicyclooctane compounds [I], they may be mixed with carriers, diluents, lubricants, fillers and/or binders such as lactose, sucrose, calcium, phosphate, starch, talcum, casein, magnesium stearate, methyl cellulose, polyglycols, tragacanth and the like, sometimes together with stabilizers and emulsifying agents. The resulting mixture may be processed in a usual manner to form tablets, capsules, pills, ampoules and the like. The daily dosage may vary depending upon the administration route; the usual oral dosage of the active ingredient is between about 1 mg and about 1000 mg daily for human beings.

Specific examples of the bicyclooctane compound [I] are as follows. All of the compounds below have four isomers, that is, $(3'\alpha, 7Z)$, $(3'\alpha, 7E)$, $(3'\beta, 7E)$ and $(3'\beta, 7Z)$.

$2\beta$-(3'-hydroxy-trans-1'-octenyl)3$\alpha$-hydroxy-7-(2''-carboxyethoxy)imino-cis-bicyclo[3,3,0]octane

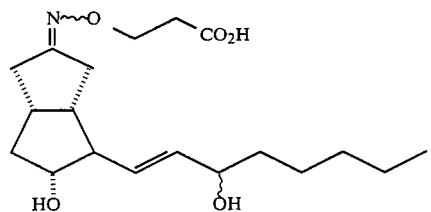

$2\beta$-(3'-hydroxy-3'-methyl-trans-1'-octenyl)3$\alpha$-hydroxy-7-(2'-carboxyethoxy)imino-cis-bicyclo[3,3,-0]octane $2\beta$-(3'-hydroxy-4',4'-dimethyl-trans-1'-octenyl)3$\alpha$-hydroxy-7-(2''-carboxyethoxy)imino-cis-bicyclo[3,3,-0]octane $2\beta$-(3'-hydroxy-5'-methyl-trans-1'-octenyl)3$\alpha$-hydroxy-7-(2''-carboxyethoxy)imino-cis-bicyclo-[3,3,0]octane $2\beta$-(3'-hydroxy-5'-methyl-trans-1'-nonenyl)3$\alpha$-hydroxy-7-(2''-carboxyethoxy)imino-cis-bicyclo-[3,3,0]octane $2\beta$-[4'-(p-fluorophenoxy)-3'-hydroxy-trans-1'-butenyl]-3$\alpha$-hydroxy-7-(2''-carboxyethoxy)imino-cis-bicyclo-[3,3,0]octane $2\beta$-[4'-(m-trifluoromethylphenoxy)3'-hydroxy-trans-1'-butenyl]3$\alpha$-hydroxy-7-(2''-carboxyethoxy)imino-cis-bicyclo[3,3,0]octane $2\beta$-(4'-phenoxy-3'-hydroxy-trans-1'-butenyl)3$\alpha$-hydroxy-7-(2''-carboxyethoxy)imino-cis-bicyclo[3,3,-0]octane $2\beta$-[4'-(p-chlorophenoxy)3'-hydroxy-trans-1'-butenyl]3$\alpha$-hydroxy-7-(2''-carboxyethoxy)imino-cis-bicyclo[3,3,0]octane $2\beta$-(4'-phenyl-3'-hydroxy-trans-1'-butenyl)3$\alpha$-hydroxy-7-(2''-carboxyethoxy)imino-cis-bicyclo[3,3,-0]octane 2β-(3'-hydroxy-4'-propoxy-trans-1'-butenyl)3α-hydroxy-7-(2''-carboxyethoxy)imino-cis-bicyclo[3,3,0]octane 2β-(3'-hydroxy-trans-1'-cis-5'-octadienyl)3α-hydroxy-7-(2''-carboxyethoxy)imino-cis-bicyclo[3,3,0]octane 2β-(4'-cyclohexyl-3'-hydroxy-trans-1'-butenyl)3α-hydroxy-7-(2''-carboxyethoxy)imino-cis-bicyclo[3,3,0]octane 2β-[4'-(m-methylphenoxy)-3'-hydroxy-trans-1'-butenyl]3α-hydroxy-7-(2''-carboxyethoxy)imino-cis-bicyclo[3,3,0]octane 2β-[4'-(m-methoxyphenoxy)-3'-hydroxy-trans-1'-butenyl]3α-hydroxy-7-(2''-carboxyethoxy)imino-cis-bicyclo[3,3,0]octane 2β-(3'-hydroxy-trans-1'-octene-5'-yn)3α-hydroxy-7-(2''-carboxyethoxy)imino-cis-bicyclo[3,3,0]octane 2β-(3'-hydroxy-3'-cyclohexyl-trans-1'-propenyl)3α-hydroxy-7-(2''-carboxyethoxy)imino-cis-bicyclo[3,3,0]octane 2β-(3'-hydroxy-trans-1'-octenyl)3α-hydroxy-7-(3''-carboxypropoxy)imino-cis-bicyclo[3,3,0]octane 2β-(3'-hydroxy-trans-1'-octenyl)-7-(2''-carboxyethoxy)imino-cis-bicyclo[3,3,0]octane 2β-(3'-hydroxy-4',4'-dimethyl-trans-1'-octenyl)-7-(2''-carboxyethoxy)imino-cis-bicyclo[3,3,0]octane 2β-[4'-(p-fluorophenoxy)3'-hydroxy-1'-transbutenyl]-7-(2''-carboxyethoxy)imino-cis-bicyclo[3,3,0]octane 2-(3'-hydroxy-trans-1'-octenyl)-7-(2''-carboxyethoxy)imino-cis-bicyclo[3,3,0]oct-2-ene 2-(3'-hydroxy-4',4'-dimethyl-trans-1'-octenyl)-7-(2''-carboxyethoxy)imino-cis-bicyclo[3,3,0]oct-2-ene 2-[4'-(p-fluorophenoxy)3'-hydroxy-trans-1'-butenyl]-7-(2''-carboxyethoxy)imino-cis-bicyclo[3,3,0]oct-2-ene 2-(4'-phenoxy-3'-hydroxy-trans-1'-butenyl)-7-(2''-carboxyethoxy)imino-cis-bicyclo[3,3,0]oct-2-ene 2-(3'-hydroxy-trans-1'-nonenyl)-7-(2''-carboxyethoxy)imino-cis-bicyclo[3,3,0]oct-2-ene 2β-(3'-hydroxy-4'-methyl-trans-1'-octen-6'-yn)-3α-hydroxy-7-(2''-carboxyethoxy)imino-cis-bicyclo[3,3,0]octane 2β-(3'-hydroxy-4'-methyl-trans-1'-octene-6'-yn)-7-(2''-carboxyethoxy)imino-cis-bicyclo[3,3,0]octane 2-(3'-hydroxy-4'-methyl-trans-1'-octene-6'-yn)-7-(2''-carboxyethoxy)imino-cis-bicyclo[3,3,0]oct-2-ene 2-(3'-hydroxy-4'-methyl-trans-1'-octenyl)-7-(2''-carboxyethoxy)imino-cis-bicyclo[3,3,0]oct-2-ene 2-(3'-hydroxy-5'-methyl-trans-1'-nonenyl)-7-(2''-carboxyethoxy)imino-cis-bicyclo[3,3,0]oct-2-ene 2β-(3'-hydroxy-trans-1'-octenyl)3α-hydroxy-7-(2''-methoxycarbonylethoxy)imino-cis-bicyclo[3,3,0]octane 2β-(3'-hydroxy-trans-1'-octenyl)-7-(2''-methoxycarbonylethoxy)imino-cis-bicyclo[3,3,0]octane 2-(3'-hydroxy-trans-1'-octenyl)-7-(2''-methoxycarbonylethoxy)imino-cis-bicyclo[3,3,0]oct-2-ene 2-(3'-hydroxy-trans-1'-octenyl)-7-(2''-aminocarbonylethoxy)imino-cis-bicyclo[3,3,0]oct-2-ene 2-(3'-hydroxy-trans-1'-octenyl)-7-(2''-piperidinocarbonylethoxy)imino-cis-bicyclo[3,3,0]oct-2-ene 2-(3'-hydroxy-trans-1'-octenyl)-7-(2''-anilinocarbonylethoxy)imino-cis-bicyclo[3,3,0]oct-2-ene 2β-(3'-hydroxyoctyl)3α-hydroxy-7-(2''-carboxyethoxy)imino-cis-bicyclo[3,3,0]octane 2β-(3'-hydroxy-4',4'-dimethyloctyl)3α-hydroxy-7-(2''-carboxyethoxy)imino-cis-bicyclo[3,3,0]octane 2β-[4'-(p-fluorophenoxy)-3'-hydroxybutyl]3α-hydroxy-7-(2''-carboxyethoxy)imino-cis-bicyclo[3,3,0]octane Practical and preferred embodiments of the present invention are illustratively shown in the following examples, which are not intended to limit the scope of the invention thereto.

REFERENTIAL EXAMPLE 1

To a mixed solution of 8-oxo-cis-bicyclo[4,3,0]nona-3-ene (10 g), ethyl alcohol (100 ml), water (20 ml) and hydroxyamine hydrochloride (20 g), was added sodium hydroxide (37 g) at room temperature. After being stirred for one hour, the reaction mixture was poured into water. The crystals were gathered by filtration and washed with water. After drying, there was obtained 8-hydroxyimino-cis-bicyclo[4,3,0]nona-3-ene.
mp. 100°–103° C.

REFERENTIAL EXAMPLE 2

To a toluene solution (20 ml) of 8-hydroxyimino-cis-bicyclo[4,3,0]nona-3-ene (1 g), was added sodium hydride (50% mineral oil dispersion, 330 mg), and the mixture was stirred for 0.5 hr at room temperature. After addition of γ-chlorobutyronitrile (5 g) to the mixture, stirring was continued for 2 hr. After cooling, the reaction mixture was poured into water and extracted with ethyl acetate. The extract was washed with water and dried over $Na_2SO_4$ and concentrated to give an oil. This material was chromatographed on silica gel to give 8-(3'-cyanopropoxy)imino-cis-bicyclo[4,3,0]nona-3-ene as an oil.
NMR δ ($CDCl_3$) 4.0 (2H, t), 5.6 (2H, s)

REFERENTIAL EXAMPLE 3

Sodium hydride (0.78 g, 60% mineral oil dispersion) was added to a benzene solution (100 ml) of 8-hydroxyimino-cis-bicyclo[4,3,0]nona-3-ene (4.24 g). After the mixture was stirred for 1 hr, β-propiolactone (2.16 ml) was added at 15°–20° C. After being stirred for 1 hr, the mixture was poured into water and separated. The aqueous layer was neutralized and extracted with ethylacetate. The ethylacetate layer was washed with water, dried and concentrated to give 8-(2'-carboxyethoxy)-imino-cis-bicyclo[4,3,0]nona-3-ene.
NMR δ ($CDCl_3$) 2.62 (2H, t), 4.2 (2H, t), 5.55 (2H, s)

This material was dissolved in methanol (30 ml) and conc. sulfuric acid was added. The mixture was stirred at room temperature, poured into aqueous sodium bicarbonate and extracted with ethylacetate. The organic layer was washed with water, dried over $Na_2SO_4$, concentrated and then chromatographed to give 8-(2'-methoxycarbonylethoxy)imino-cis-bicyclo[4,3,0]nona-3-ene as an oil.
NMR δ ($CDCl_3$) 2.62 (2H, t), 3.67 (3H, s), 4.24 (2H, t), 5.63 (2H, s).

REFERENTIAL EXAMPLE 4

A methanol solution (160 ml) of 8-(2'-methoxycarbonylethoxy)-imino-cis-bicyclo[4,3,0]nona-3-ene (4.5 g) was subjected to a stream of ozonized oxygen at −50° to −60° C. After the starting material had disappeared, dimethylsulfide (120 ml) was added and the mixture was stirred for 2 hr at −20° C. to 0° C. The mixture was then concentrated by introduction of a stream of nitrogen to given an oily dialdehyde.

The dialdehyde thus obtained was dissolved in methanol (150 ml) and an aqueous sodium hydroxide (1%, 60 ml) was added at 5° C. to 10° C. The mixture was stirred for 15 minutes at the same temperature and then poured into a mixture of water and ethylacetate. After separation, the organic layer was washed with water, dried and concentrated under reduced pressure to give an oily 2β-formyl-3α-hydroxy-7-(2-methoxycarbonylethoxy)-imino-cis-bicyclo[3,3,0]octane.

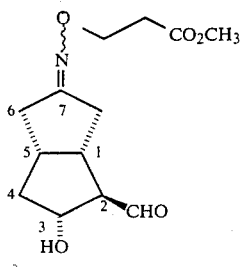

A tetrahydrofuran solution (THF, 20 ml) of the aldol (4.0 g) obtained above was added to a THF solution (425 ml) of the ylide prepared with dimethyl-2-oxo-heptyl phosphonate (9.5 g) and sodium hydride (60%, 1.14 g). The mixture was stirred for 1 hr at room temperature, and then poured into water, and extracted with ethylacetate. The extract was washed with water, dried and concentrted under reduced pressure and then chromatographed on silca gel to give two oily isomers.

2β-(3′-oxo-trans-1′-octenyl)-3α-hydroxy-7Z-(2″-methoxycarbonylethoxy)-imino-cis-bicyclo[3,3,0]octane

| NMR δ (CDCl₃) | 0.88 (3H, t like), 3.7 (3H, s), 4.2 (2H, t), 6.1 (1H, d), 6.7 (1H, d, d) | 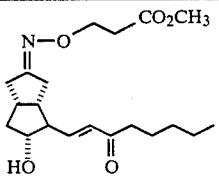 |

2β-(3′-oxo-trans-1′-octenyl)-3α-hydroxy-7E-(2″-methoxycarbonylethoxy)-imino-cis-bicyclo[3,3,0]octane

| NMR δ (CDCl₃) | 0.88 (3H, t like), 3.63 (3H, s), 4.15 (2H, t), 6.08 (1H, d), 6.65 (1H, d, d) | 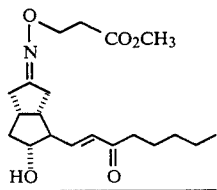 |

REFERENTIAL EXAMPLE 5

In the same manner as Referential Example 4, there were obtained the following compounds.

2β-(3′-oxo-4′,4′-dimethyl-trans-1′-octenyl)-3α-hydroxy-7E-(2″-methoxycarbonylethoxy)-imino-cis-bicyclo[3,3,0]octane NMR δ (CDCl₃) 0.87 (3H, t-like), 3.63 (3H, s), 4.17 (2H, t), 6.35–6.8 (2H, m).

2β-(3′-oxo-4′,4′-dimethyl-trans-1′-octenyl)-3α-hydroxy-7Z-(2″-methoxycarbonylethoxy)-imino-cis-bicyclo-[3,3,0]octane NMR δ (CDCl₃) 0.87 (3H, t-like), 3.63 (3H, s), 4.17 (2H, t), 6.35–6.9 (2H, m).

2β-[4′-(p-fluorophenoxy)-3′-oxo-trans-1′-butenyl]-3α-hydroxy-7E-(2″-methoxycarbonylethoxy)-imino-cis-bicyclo-[3,3,0]octane NMR δ (CDCl₃) 3.63 (3H, s), 4.27 (2H, t), 4.67 (2H, s), 6.45 (1H, d), 6.65–7.2 (5H, m)

2β-[4′-(p-fluorophenoxy)-3′-oxo-trans-1′-butenyl]-3α-hydroxy-7Z-(2″-methoxycarbonylethoxy)-imino-cis-bicyclo-[3,3,0]octane NMR δ (CDCl₃) 3.65 (3H, s), 4.23 (2H, t), 4.63 (2H, s), 6.38 (1H, d), 6.6–7.1 (5H, m)

2β-(4′-methyl-3′-oxo-trans-1′-pentenyl)-3α-hydroxy-7E-(2″-methoxycarbonylethoxy)-imino-cis-bicyclo[3,3,0]octane NMR δ (CDCl₃) 1.13 (6H, d), 3.7 (3H, s), 4.28 (2H, t), 6.27 (1H, d), 6.8 (1H, d,d).

2β-(4′-methyl-3′-oxo-trans-1′-octen-6′-ynyl)-3α-hydroxy-7E-(2″-methoxycarbonylethoxy)-imino-cis-bicyclo[3,3,0]octane NMR δ (CDCl₃) 1.18 (3H, d), 1.75 (3H, s), 3.7 (3H, s), 4.27 (2H, t), 6.27 (1H, d), 6.83 (1H, d,d).

REFERENTIAL EXAMPLE 6

A methanol solution (160 ml) of 8-(2′methoxycarbonylethoxy)-imino-cis-bicyclo-[4,3,0]-nona-3-ene (4.5 g) was subjected to a stream of ozonized oxygen at −50° to −60° C. After the starting material had disappeared, dimethylsulfide (120 ml) was added and the mixture was stirred for 2 hr at −20° to 0° C. The mixture was then concentrated by introduction of a stream of nitrogen to give an oily dialdehyde.

The dialdehyde thus obtained was dissolved in methanol (250 ml) and potassium carbonate (2.5 g) was added at room temperature. The mixture was stirred for 2.5 hr and was poured into water and then extracted with ethyl acetate.

The extract was washed with water, dried and concentrated under reduced pressure to give 2-formyl-7-(2″-methoxycarbonylethoxy)-imino-cis-bicyclo-[3,3,0]oct-2-ene.

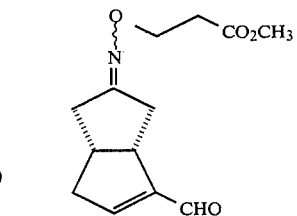

A tetrahydrofuran solution (75 ml) of the aldehyde (3.5 g) obtained above was added to a tetrahydrofuran solution (425 ml) of the ylide prepared with dimethyl-2-oxo-heptylphosphonate (9.5 g) and sodium hydride (60%, 1.14 g). The mixture was stirred for 2 hr at room temperature and poured into water and then extracted with ethylacetate. The organic layer was washed with water, dried, concentrated under reduced pressure and then chromatographed to give 2-(3′-oxo-trans-1′-octenyl)-7E-(2″-methoxycarbonylethoxy)-imino-cis-bicyclo-[3,3,0]oct-2-ene.

NMR δ (CDCl₃) 0.88 (3H, t-like), 3.62 (3H, s), 4.13 (2H, t), 5.8–6.25 (2H, m), 7.17 (1H, d) and 7Z isomer.

NMR δ (CDCl₃) 0.87 (3H, t), 3.67 (3H, s), 4.23 (2H, t), 5.9–6.1 (2H, d like) 7.27 (1H, d)

REFERENTIAL EXAMPLE 7

According to the same procedures as Referential Example 6, there were obtained the following compounds.

2-(3'-oxo-4',4'-dimethyl-trans-1'-octenyl)-7E-(2''-methoxycarbonylethoxy)-imino-cis-bicyclo-[3,3,0]oct-2-ene.

NMR δ (CDCl$_3$) 0.87 (3H, t like), 3.72 (3H, s), 4.29 (2H, t).

2-(3'-oxo-4'-methyl-trans-1'-pentenyl)-7E-(2''-methoxycarbonylethoxy)-imino-cis-bicyclo-[3,3,0]oct-2-ene.

NMR δ (CDCl$_3$) 1.13 (6H, d), 3.7 (3H, s), 4.38 (2H, t).

2-(3'-oxo-2'-methyl-trans-1'-octenyl)-7Z-(2''-methoxycarbonylethoxy)-imino-cis-bicyclo-[3,3,0]oct-2-ene.

NMR δ (CDCl$_3$) 0.7 (3H, t like), 1.93 (3H, s), 3.7 (3H, s), 4.27 (2H, t), 5.93 (1H, s), 6.93 (1H, s).

2-(2'-methyl-3'-oxo-trans-1'-octenyl)-7E-(2''-methoxycarbonylethoxy)-imino-cis-bicyclo-[3,3,0]oct-2-ene.

NMR δ (CDCl$_3$) 0.89 (3H, t like), 3.62 (3H, s), 4.25 (2H, t).

2-(3'-oxo-4'-methyl-trans-1'-octen-6'-ynyl)-7E-(2''-methoxycarbonyethoxy)-imino-cis-bicyclo-[3,3,0]oct-2-ene.

NMR δ (CDCl$_3$) 1.17 (3H, d), 1.74 (3H, s), 3.68 (3H, s), 4.27 (2H, t).

REFERENTIAL EXAMPLE 8

In the same manner as Referential Example 4, using 8-(3'-cyanopropoxy)-imino-cis-bicyclo-[4,3,0]nona-3-ene obtained in Referential Example 2, there were obtained two isomers.

2β-(3'-oxo-trans-1'-octenyl)-3α-hydroxy-7Z-(3''-cyanopropoxy)-imino-cis-bicyclo-[3,3,0]octane NMR δ (CDCl$_3$) 0.87 (3H, t), 4.1 (2H, t) 6.18 (1H, d), 6.75 (1H, d, d).

2β-(3'-oxo-trans-1'-octenyl)-3α-hydroxy-7E-(3''-cyanopropoxy)-imino-cis-bicyclo-[3,3,0]octane NMR δ (CDCl$_3$) 0.88 (3H, t-like), 4.1 (2H, t), 6.17 (1H, d), 6.75 (1H, d, d).

REFERENTIAL EXAMPLE 9

To an ethanol solution (20 ml) of 2β-(3'-oxo-trans-1'-octenyl)-3α-hydroxy-7Z-(3''-cyanopropoxy)-imino-cis-bicyclo-[3,3,0]octane (110 mg) was added sodium borohydride (300 mg) at −20° to −40° C. under nitrogen. The mixture was stirred for 2 hr at the same temperature and poured into water and then extracted with ethylacetate. The extract was washed with water, dried and concentrated to give an oily 2β-(3'-hydroxy-trans-1'-octenyl)-3α-hydroxy-7Z-(3''-cyanopropoxy)-imino-cis-bicyclo-[3,3,0]octane.

NMR δ (CDCl$_3$) 0.88 (3H, t-like), 4.08 (2H, t), 5.4–5.75 (2H, m)

REFERENTIAL EXAMPLE 10

According to the same procedures as Referential Example 9, there was obtained 2β-(3'-hydroxy-trans-1'-octenyl)-3α-hydroxy-7E-(3''-cyanopropoxy)-imino-cis-bicyclo-[3,3,0]octane as an oil.

NMR δ (CDCl$_3$) 0.88 (3H, t-like), 4.08 (2H, t), 5.4–5.75 (2H, m)

REFERENTIAL EXAMPLE 11

A mixture of 2β-(3'-oxo-trans-1'-octenyl)-3α-hydroxy-7E-(2''-methoxycarbonylethoxy)-imino-cis-bicyclo-[3,3,0]octane (120 mg), 10% Palladium on charcoal (100 mg), water (300 mg) and ethanol (20 ml) was stirred under an atomosphere of hydrogen at room temperature. The mixture was filtered and washed with ethanol. The filtrate was condensed under reduced pressure to give 2β-(3'-oxo-octyl)-3α-hydroxy-7E-(2''-methoxycarbonylethoxy)-imino-cis-bicyclo-[3,3,0]octane NMR δ (CDCl$_3$) 0.9 (3H, t), 3.72 (3H, s), 4.3 (2H, t)

EXAMPLE 1

To an ethanol solution (50 ml) of 2β-(3'-oxo-trans-1'-octenyl)-3α-hydroxy-7E-(2''-methoxycarbonylethoxy)-imino-cis-bicyclo-[3,3,0]octane (475 mg) was added sodium borohydride (1 g) at −50° C., and the mixture was stirred for 2 hr at −50° to −20° C. After the starting material had disappeared, the mixture was poured into water and extracted with ethyl acetate. The extract was washed with water, dried, concentrated at reduced pressure and then chromatographed to give 2β-(3'α-hydroxy-trans-1'-octenyl)-3α-hydroxy-7E-(2''-methoxycarbonylethoxy)-imino-cis-bicyclo-[3,3,0]octane.

NMR δ (CDCl$_3$) 0.7–1.1 (3H, br), 3.68 (3H, s), 4.28 (2H, t), 5.4–5.6 (2H, m)

and 2β-(3'β-hydroxy-trans-1'-octenyl)-3α-hydroxy-7E-(2''-methoxycarbonylethoxy)-imino-cis-bicyclo-[3,3,0]octane NMR δ (CDCl$_3$) 0.7–1.0 (3H, br), 3.68 (3H, s), 4.28 (2H, t), 5.45–5.65 (2H, m).

EXAMPLE 2

Sodium borohydride (500 mg) was added to an ethanol solution (25 ml) of 2β-(3'-oxo-4',4'-dimethyl-trans-1'-octenyl)-3α-hydroxy-7E-(2''-methoxycarbonylethoxy)-imino-cis-bicyclo-[3,3,0]octane (200 mg) at −45° C., and the mixture was stirred for 2 hr at −20° to −45° C. After the reaction was over, the mixture was poured into water, and extracted with ethyl acetate. The extract was washed with water, dried and concentrated at reduced pressure to give 2β-(3'-hydroxy-4',4'-dimethyl-trans-1'-octenyl)-3α-hydroxy-7E-(2''-methoxycarbonylethoxy)-imino-cis-bicyclo-[3,3,0]octane as an oil.

NMR δ (CDCl$_3$) 2.63 (2H, t), 3.68 (3H, s), 0.7–1.0 (9H, m), 4.27 (2H, t), 5.4–5.7 (2H, m).

EXAMPLE 3

Lithium triisobutylborohydride (1 ml, 1M solution in THF) was added to a THF solution (25 ml) of 2β-(3'-oxo-4'-methyl-trans-1'-octen-6'-ynyl)-3α-hydroxy-7E-(2''-methoxycarbonylethoxy)-imino-cis-bicyclo-[3,3,0]octane (260 mg) at −50° to −60° C. The mixture was stirred for 1 hr at the same temperature, and then poured into water and extracted with ethyl acetate. The extract was washed with water, dried, concentrated and then chromatographed to give 2β-(3'α-hydroxy-4'-methyl-trans-1'-octen-6'-ynyl)-3α-hydroxy-7E-(2''-methoxycarbonylethoxy)-imino-cis-bicyclo-[3,3,0]octane NMR δ (CDCl$_3$) 1.77 (3H, s) 3.68 (3H, s) 4.28 (2H, t), 5.47–5.68 (2H, m).

and 2β-(3'β-hydroxy-4'-methyl-trans-1'-octen-6'-ynyl)-3α-hydroxy-7E-(2''-methoxycarbonylethoxy)-imino-cis-bicyclo-[3,3,0]octane NMR δ (CDCl$_3$) 0.97 (3H, d), 1.78 (3H, s), 3.7 (3H, s), 4.28 (2H, t), 5.5–5.8 (2H, br).

EXAMPLE 4

A mixture of 2β-(3'-hydroxy-trans-1'-octenyl)-3α-hydroxy-7E-(3''-cyanopropoxy)-imino-cis-bicyclo-

[3,3,0]octane (61 mg), potassium hydroxide (1 g), water (4 ml) and ethanol (12 ml) was refluxed for 7 hr. After cooling, the mixture was poured into water and extracted with ethyl ether. The aqueous layer was acidified with acetic acid and extracted with ethyl acetate. The ethyl acetate layer was washed with water, dried and concentrated to give 2β-(3'-hydroxy-trans-1'-octenyl)-3α-hydroxy-7E-(3''-carboxypropoxy)-imino-cis-bicyclo-[3,3,0]octane as an oil.

NMR δ (CDCl$_3$) 0.7–1.0 (3H, br), 4.07 (2H, t-like), 4.9–5.8 (5H, br).

EXAMPLE 5

A mixture of 2β-(3'β-hydroxy-trans-1'-octenyl)-3α-hydroxy-7E-(2''-methoxycarbonylethoxy)-imino-cis-bicyclo-[3,3,0]octane (60 mg), potassium hydroxide (1 g), methanol (10 ml) and water (10 ml) was stirred for 1 hr at room temperature and poured into water and then extracted with ethyl ether. The aqueous layer was acidified with acetic acid and extracted with ethyl acetate. The ethyl acetate layer was washed with water, dried, concentrated under reduced pressure to give 2β-(3'β-hydroxy-trans-1'-octenyl)-3α-hydroxy-7E-(2''-carboxyethoxy)-imino-cis-bicyclo-[3,3,0]octane NMR δ (CDCl$_3$) 0.7–1.1 (3H, br), 4.28 (2H, t), 5.35–5.9 (5H, br).

EXAMPLE 6

According to the same procedures as Example 1 or Example 2, there were obtained the following compounds.

2β-(3'-hydroxy-trans-1'-octenyl)-3α-hydroxy-7Z-(2''-methoxycarbonylethoxy)-imino-cis-bicyclo-[3,3,0]octane NMR δ (CDCl$_3$) 3.7 (3H, s), 4.27 (2H, t), 5.4–5.8 (2H, br).

2β-(3'-hydroxy-4'-methyl-trans-1'-pentenyl)-3α-hydroxy-7E-(2''-methoxycarbonylethoxy)-imino-cis-bicyclo-[3,3,0]octane NMR δ (CDCl$_3$) 0.7–1.0 (6H, m), 3.7 (3H, s), 4.25 (2H, t), 5.4–5.8 (2H, br).

2-(3'-hydroxy-4',4'-dimethyl-trans-1'-octenyl)7E-(2''-methoxycarbonylethoxy)-imino-cis-bicyclo-[3,3,0]oct-2-ene NMR δ (CDCl$_3$) 0.7–1.0 (9H, br), 3.68 (3H, s), 4.27 (2H, t).

2-(2'-methyl-3'-hydroxy-trans-1'-octenyl)-7Z-(2''-methoxycarbonylethoxy)-imino-cis-bicyclo-[3,3,0]oct-2-ene NMR δ (CDCl$_3$) 3.68 (3H, s), 4.25 (2H, t), 5.53 (1H, br), 5.82 (1H, br).

2-(3'-hydroxy-trans-1'-octenyl)-7Z-(2''-methoxycarbonylethoxy)-imino-cis-bicyclo[3,3,0]oct-2-ene NMR δ (CDCl$_3$) 0.7–1.0 (3H, br), 3.67 (3H, s), 4.23 (2H, t), 5.3–5.7 (3H, br).

2β-(3'-hydroxy-4',4'-dimethyl-trans-1'-octenyl)-3α-hydroxy-7Z-(2''-methoxycarbonylethoxy)-imino-cis-bicyclo[3,3,0]octane NMR δ (CDCl$_3$) 3.7 (3H, s), 4.27 (2H, t), 5.4–5.75 (2H, m).

2-(3'-hydroxy-trans-1'-octenyl)-7E-(2''-methoxycarbonylethoxy)-imino-cis-bicyclo[3,3,0]oct-2-ene NMR δ (CDCl$_3$) 0.88 (3H, t like), 3.67 (3H, s), 4.26 (2H, t), 5.5–5.85 (3H, m).

2-(3'-hydroxy-4'-methyl-trans-1'-pentenyl)-7E-(2''-methoxycarbonylethoxy)-imino-cis-bicyclo[3,3,0]oct-2-ene NMR δ (CDCl$_3$) 0.92 (6H, d), 3.67 (3H, s), 4.15 (2H, t).

2-(2'-methyl-3'-hydroxy-trans-1'-octenyl)-7E-(2''-methoxycarbonylethoxy)-imino-cis-bicyclo[3,3,0]oct-2-ene NMR δ (CDCl$_3$) 0.73–1.03 (3H, br), 3.67 (3H, s), 4.27 (2H, t).

2-(3'-hydroxy-4'-methyl-trans-1'-octen-6'-ynyl)-7E-(2''-methoxycarbonylethoxy)-imino-cis-bicyclo[3,3,0]oct-2-ene NMR δ (CDCl$_3$) 0.96 (3H, d), 1.75 (3H, s), 3.65 (3H, s), 4.25 (2H, t), 5.5–6.0 (3H, m).

2β-[3'-hydroxy-4'-(p-fluorophenoxy)-trans-1'-butenyl]-3α-hydroxy-7Z-(2''-methoxycarbonylethoxy)-imino-cis-bicyclo[3,3,0]octane NMR δ (CDCl$_3$) 3.67 (3H, s), 3.7–3.9 (3H, br), 4.27 (2H, t), 5.63–5.77 (2H, m), 6.63–7.1 (4H, m).

2β-[3'-hydroxy-4'-(p-fluorophenoxy)-trans-1'-butenyl]-3α-hydroxy-7E-(2''-methoxycarbonylethoxy)-imino-cis-bicyclo[3,3,0]octane NMR δ (CDCl$_3$) 3.7 (3H, s), 4.27 (2H, t), 5.6–5.8 (2H, m), 6.6–7.1 (4H, m).

EXAMPLE 7

In the same manner as Example 5, there were obtained the following compounds.

2β-(3'α-hydroxy-trans-1'-octenyl)-3α-hydroxy-7E-(2''-carboxyethoxy)-imino-cis-bicyclo[3,3,0]octane NMR δ (CDCl$_3$) 0.7–1.0 (3H, m), 4.31 (2H, t), 4.6–5.1 (3H, br), 5.33–5.6 (2H, m).

2β-(3'-hydroxy-4',4'-dimethyl-trans-1'-octenyl)-3α-hydroxy-7E-(2''-carboxyethoxy)-imino-cis-bicyclo[3,3,0]octane NMR δ (CDCl$_3$) 0.7–1.0 (9H, br), 3.6–4.1 (2H, br), 4.27 (2H, t), 5.45–5.75 (2H, br) 6.1–6.5 (3H, br).

2β-(3'α-hydroxy-4'-methyl-trans-1'-octen-6'-ynyl)-3α-hydroxy-7E-(2''-carboxyethoxy)-imino-cis-bicyclo[3,3,0]octane NMR δ (CDCl$_3$) 1.78 (3H, s), 4.33 (2H, t), 5.1–5.7 (5H, br).

2β-(3'β-hydroxy-4'-methyl-trans-1'-octen-6'-ynyl)-3α-hydroxy-7E-(2''-carboxyethoxy)-imino-cis-bicyclo[3,3,0]octane NMR δ (CDCl$_3$) 1.78 (3H, s), 4.32 (2H, t) 5.3–5.8 (2H, br).

2β-(3'-hydroxy-trans-1'-octenyl)-3α-hydroxy-7Z-(2''-carboxyethoxy)-imino-cis-bicyclo[3,3,0]octane NMR δ (CDCl$_3$) 0.7–1.1 (3H, br), 4.27 (2H, t like) 5.4–5.75 (2H, br), 6.6–7.2 (3H, br).

2β-(3'-hydroxy-4',4'-dimethyl-trans-1'-octenyl)-3α-hydroxy-7Z-(2''-carboxyethoxy)-imino-cis-bicyclo[3,3,0]octane NMR δ (CDCl$_3$) 0.6–1.0 (9H, br), 3.5–4.0 (2H, br), 4.28 (2H, t like), 5.3–6.1 (5H, br).

2-(3'-hydroxy-trans-1'-octenyl)-7E-(2''-carboxyethoxy)-imino-cis-bicyclo[3,3,0]oct-2-ene NMR δ (CDCl$_3$) 0.7–1.0 (3H, br), 4.27 (2H, t like), 5.3–5.8 (3H, br), 5.8–6.3 (2H, br).

2β-(3'-hydroxy-4'-methyl-trans-1'-pentenyl)-3α-hydroxy-7E-(2''-carboxyethoxy)-imino-cis-bicyclo[3,3,0]octane NMR δ (CDCl$_3$) 0.73–1.0 (6H, br), 3.5–4.0 (2H, m) 4.18 (2H, t), 5.45–5.8 (2H, br)

2-(2'-methyl-3'-hydroxy-trans-1'-octenyl)-7E-(2''-carboxyethoxy)-imino-cis-bicyclo[3,3,0]oct-2-ene NMR δ (CDCl$_3$) 0.7–1.1 (3H, br), 1.65 (3H, s), 4.3 (2H, t).

2-(3'-hydroxy-4'-methyl-trans-1'-octen-6'-ynyl)-7E-(2''-carboxyethoxy)-imino-cis-bicyclo[3,3,0]oct-2-ene NMR δ (CDCl$_3$) 1.77 (3H, br), 4.0.

2β-[3'-hydroxy-4'-(p-fluorophenoxy)-trans-1'-butenyl]-3α-hydroxy-7E-(2''-carboxyethoxy)-imino-cis-bicyclo[3,30]octane NMR δ (CDCl$_3$) 3.6–4.0 (3H, m), 4.17 (2H, t), 4.3–4.6 (1H, br), 5.6–5.8 (2H, br), 6.7–7.1 (4H, m).

2β-[3'-hydroxy-4'-(p-fluorophenoxy)-trans-1'-butenyl]-3α-hydroxy-7Z-(2''-carboxyethoxy)-imino-cis-bicyclo[3,3,0]octane NMR δ (CDCl$_3$) 3.4–4.1 (3H, br), 4.1–4.6 (3H, m), 5.5–5.8 (2H, br).

EXAMPLE 8

Sodium borohydride (200 mg) was added to a methanol solution (20 ml) of 2β-(3'-oxo-octyl)-3α-hydroxy-7E-(2''-methoxycarbonylethoxy)-imino-cis-bicyclo[3,3,0]octane (120 mg) at room temperature. The mixture was stirred for 1 hr and poured into water and then extracted with ethyl acetate. The extract was washed with water, dried and concentrated at reduced pressure to give an oily 2β-(3'-hydroxyoctyl)-3α-hydroxy-7E-(2''-methoxycarbonylethoxy)-imino-cis-bicyclo[3,3,0]octane.

NMR δ (CDCl$_3$) 0.7–1.07 (3H, br), 3.7 (3H, s), 4.28 (2H, t).

EXAMPLE 9

According to the same procedures as Example 5, using 2β-(3'-hydroxy-octyl)-3α-hydroxy-7E-(2''-methoxycarbonylethoxy)-imino-cis-bicyclo[3,3,0]octane obtained in Example 8, there was obtained 2β-(3'-hydroxyoctyl)-3α-hydroxy-7E-(2''-carboxyethoxy)-imino-cis-bicyclo[3,3,0]octane NMR δ (CDCl$_3$) 0.7–1.0 (3H, br), 3.4–4.0 (2H, br), 4.3 (2H, t), 6.2–6.6 (3H, br).

EXAMPLE 10

In the same manner as Example 4, there was obtained 2β-(3'-hydroxy-trans-1'-octenyl)-3α-hydroxy-7Z-(3''-carboxypropoxy)-imino-cis-bicyclo[3,3,0]octane NMR δ (CDCl$_3$) 0.7–1.1 (3H, br), 4.03 (2H, t like) 4.8–5.8 (5H, m).

What is claimed is:

1. A compound of the formula

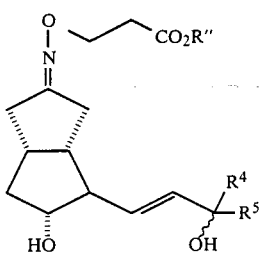

wherein R'' is a hydrogen atom or a $C_1$–$C_4$ alkyl group, and $R^4$ is a hydrogen atom or a $C_1$–$C_4$ alkyl group, $R^5$ is a hydrogen atom, a $C_3$–$C_8$ alkynyl group, a $C_3$–$C_8$ alkenyl group, a $C_1$–$C_8$ alkyl group, a $C_3$–$C_7$ cycloalkyl group, a hydroxy $C_1$–$C_8$ alkyl group or a group of the formula: —$(CH_2)_m$-B (m is 1 or 2 and B is a $C_1$–$C_4$ alkoxy, a $C_3$–$C_7$ cycloalkyl, or a phenyl or phenoxy group optionally substituted with a halogen atom, a $C_1$–$C_4$ alkyl group, a trifluoromethyl group or a $C_1$–$C_4$ alkoxy group).

2. The compound according to claim 1, wherein R'' is a hydrogen atom.

3. The compound according to claim 1, wherein R'' and $R^4$ are each a hydrogen atom.

4. 2β-(3'α-hydroxy-trans-1'-octenyl)3α-hydroxy-7E-(2''-carboxyethoxy)imino-cis-bicyclo[3,3,0]octane, and its stereoisomers.

5. 2β-(3'α-hydroxy-4',4'-dimethyl-trans-1'-octenyl)-3α-hydroxy-7E-(2''-carboxyethoxy)imino-cis-bicyclo[3,3,0]octane, and its stereoisomers.

* * * * *